United States Patent [19]

Sutherland et al.

[11] Patent Number: 5,059,172

[45] Date of Patent: Oct. 22, 1991

[54] SYRINGE WITH TWO PART MASTITIS CANNULA CAP

[75] Inventors: Stephen F. Sutherland, Fort Dodge, Iowa; Jerome Silverstein, North Franklin, Conn.

[73] Assignee: American Home Products, New York, N.Y.

[21] Appl. No.: 338,893

[22] Filed: Apr. 14, 1989

Related U.S. Application Data

[63] Continuation-in-part of Ser. No. 212,026, Jun. 23, 1988, Pat. No. 4,850,970, which is a continuation of Ser. No. 30,322, Mar. 26, 1987, abandoned.

[51] Int. Cl.[5] .................... A61M 1/06

[52] U.S. Cl. .................... 604/73; 604/117; 604/192; 604/278

[58] Field of Search .................... 604/54, 73, 117, 192, 604/263, 278, 198

[56] References Cited

U.S. PATENT DOCUMENTS

| | | | |
|---|---|---|---|
| 2,529,836 | 11/1950 | Darlington | 604/192 |
| 2,848,997 | 8/1958 | Miskel et al. | 604/192 |
| 2,848,998 | 8/1958 | Bryan | 604/192 |
| 2,869,545 | 1/1959 | Forsyth | 604/192 |
| 3,073,307 | 1/1963 | Stevens | 604/192 |
| 3,380,450 | 4/1968 | Adelberger | 604/192 X |
| 3,434,473 | 3/1969 | Smith | 604/117 |
| 4,022,191 | 5/1977 | Jamshidi | 604/117 X |
| 4,248,228 | 2/1981 | Silver | 604/192 |
| 4,453,935 | 6/1984 | Newton | 604/197 |
| 4,657,535 | 4/1987 | Nishimura et al. | 604/263 |
| 4,660,570 | 4/1987 | Dombrowski | 128/765 |
| 4,710,171 | 12/1987 | Rosenberg | 604/117 |
| 4,799,927 | 1/1989 | Davis et al. | 604/192 |
| 4,804,372 | 2/1989 | Laico et al. | 604/198 |
| 4,846,801 | 7/1989 | Okuda et al. | 604/218 |
| 4,846,811 | 7/1989 | Vanderhoof | 604/263 |
| 4,850,970 | 7/1989 | Sutherland | 604/117 |
| 4,917,679 | 4/1990 | Kronner | 604/198 |
| 5,009,640 | 4/1991 | Pyret et al. | 604/117 |

FOREIGN PATENT DOCUMENTS

| | | | |
|---|---|---|---|
| 78000 | 8/1954 | Denmark | 604/117 |

OTHER PUBLICATIONS

"Dry Treatment Technique May Affect Infection Rate", *Dairy*, May 10, 1986, vol. 42, No. 6.

"How You Infuse Cows Can Spread Mastitis", S. C. Nickerson and R. L. Boddie, *Hoards Dairyman*, Nov. 10, 1985.

*Primary Examiner*—John D. Yasko

*Assistant Examiner*—Adam J. Cermak

*Attorney, Agent, or Firm*—Darby & Darby

[57] ABSTRACT

A two part mastitis cannula cap includes an outer cap and an inner cap. The inner cap is not as long as the cannula so that a free end of the cannula protrudes beyond an end face of the inner cap. This cannula protrusion is covered by the outer cap which is securable about the free end of the inner cap. Controlled depth partial insertion of the cannula into the teat canal of a dairy cow can be accomplished by removal of only the outer cap. Alternatively, full depth cannula insertion is accomplishable upon removal of the two parts of the cap. In one embodiment, a snap-off outer cap is used. In a second embodiment, a twist-off or breakaway outer cap is utilized.

13 Claims, 2 Drawing Sheets

FIG 1
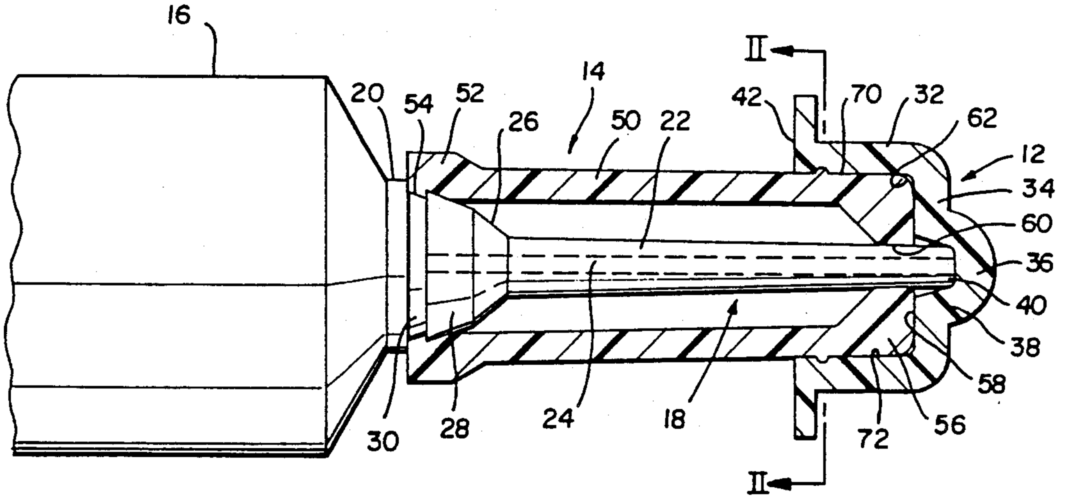
FIG 2
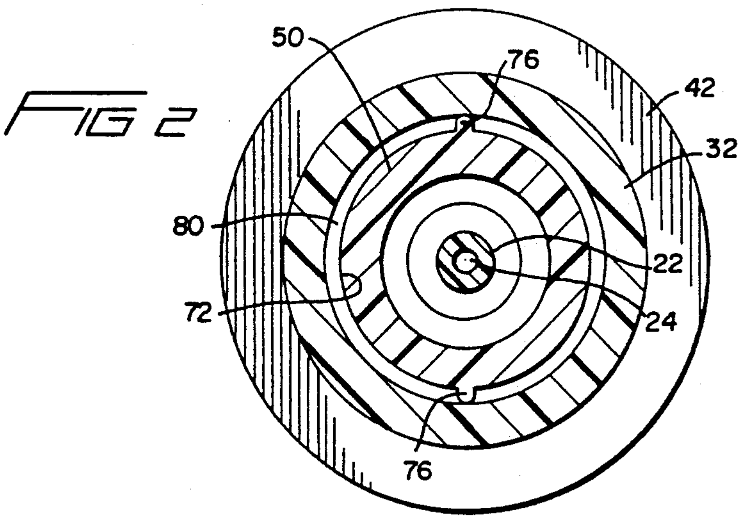
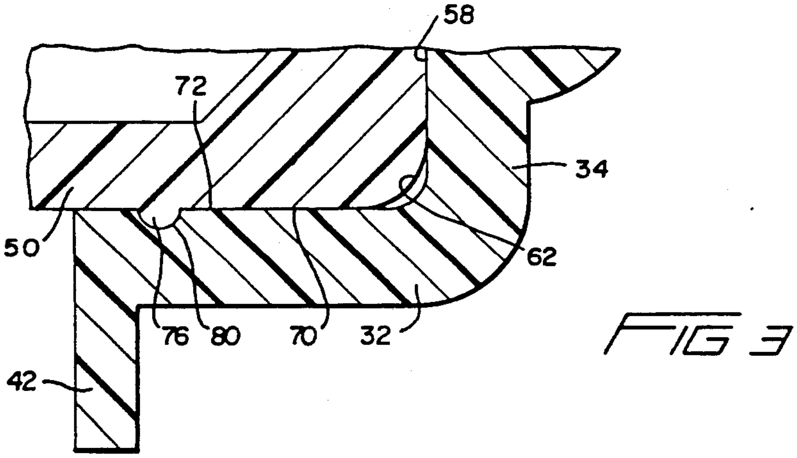
FIG 3

SYRINGE WITH TWO PART MASTITIS CANNULA CAP

CROSS REFERENCE TO RELATED APPLICATIONS

This application is a continuation-in-part of U.S. application Ser. No. 212,026 filed June 23, 1988, now U.S. Pat. No. 4,850,970 which, in turn, is a continuation of U.S. application Ser. No. 030,322, filed Mar. 26, 1987, now abandoned.

FIELD OF THE INVENTION

The present invention is directed generally to a two part cap for a cannula. More particularly, the present invention is directed to a two part cap for the cannula of a mastitis infusion syringe. Most specifically, the present invention is directed to a two part, separable, mastitis infusion cannula cap which is usable to limit the cannula's insertion depth into the teat canal of a dairy cow. The two part mastitis cannula cap includes an outer or overcap which is positioned at a free or distal end of an elongated inner cap. The outer cap is dimensioned to expose only a portion of the mastitis syringe cannula when this outer cap is removed from the inner cap. This insures that the cannula's insertion depth can be effectively limited to less than the length of the teat canal when only the outer cap is removed. Bacteria thus cannot be carried into the teat cistern and no damage occurs to the teat canal by the mastitis treatment cannula equipped with the two part cap when only the outer cap is removed.

DESCRIPTION OF THE PRIOR ART

Bovine mastitis is a serious problem which afflicts large numbers of dairy cows. This mastitis, or inflammation of the cow's mammary gland, strikes substantial percentages of cows in dairy herds and has a detrimental effect on milk production and herd profitability. The generally followed method of treatment for bovine mastitis has been the administration of various antibiotic preparations into the cow's udder through the teat canal. A mastitis infusion syringe, which carries the antibiotic preparation, typically is equipped with an insertion cannula having a length of 20 to 30 mm. This cannula and syringe assembly is provided from the antibiotic supplier as a molded plastic, disposable unit which is prefilled with the treatment antibiotic. A single piece plastic cover, which typically snap fits onto the hub of the syringe at the base of the cannula, is used to cover the cannula prior to use. At the time of treatment, the protective cap is removed from the mastitis treatment syringe cannula and the cannula end is inserted into the cow's teat end, passed through the teat canal, and positioned within the teat cistern. Once the cannula has been so positioned, the syringe is utilized to deposit the treatment antibiotic directly into the cow's teat cistern.

Recent studies have suggested that the previously practiced full cannula insertion technique may actually reduce rather than enhance the effectiveness of the treatment. This research has indicated that in some instances bacteria infecting the keratin lining of the teat canal are carried into the teat cistern by the mastitis cannula during full cannula insertion. Once these bacteria enter the teat cistern, they may produce mastitis. The cow's teat canal is approximately 5 to 10 mm in length and has a very narrow lumen (0.4–1.63 mm). This narrow canal helps to prevent bacteria from entering the cow's udder. Some bacteria may survive in the keratin lining and secretions in the distal teat canal but are prevented by the healthy teat canal from traveling the full length of the canal. These bacteria may be aided in their travel up the teat canal by the cannula as it passes through the canal during full cannula insertion. It has also been found that the teat canal or duct keratin layer, which helps control bacterial penetration into the udder, may be damaged by full cannula insertion. This full length cannula insertion may also cause the full length of the teat canal lumen to become dilated thus allowing increased bacterial travel and penetration into the teat cistern and mammary gland. Bacteria which might otherwise exist for months in the distal teat canal keratin without causing mastitis might enter the teat cistern area during full cannula insertion, serving as a source of a mastitis infection.

As a result of these above-discussed studies, there is now being utilized a partial insertion technique wherein the mastitis cannula is inserted into the teat end and up the teat canal only to a depth of generally about 3 to 4 mm. This technique appears to be beneficial in the treatment of mastitis but has made treatment procedures more difficult and time consuming for the dairyman. It is necessary that the cannula insertion depth be limited to generally about 3 to 4 mm to avoid the teat canal keratin damage, to avoid dilating the entire teat canal, and, to prevent the transport of bacteria from the distal teat canal into the teat cistern—all factors which may frequently be related to the full insertion of syringe cannulas and may be prevented by limiting cannula insertion depth to approximately 3 to 4 mm.

There presently exist no commercially available, readily usable yet disposable mastitis infusion syringe assembly which allows the user to quickly and easily control the depth of cannula insertion, thus rendering this partial insertion treatment effective. Individual measurements of each insertion depth are time consuming and are apt to be inaccurate. Mere guessing is even less accurate and may make the treatment of little value. It will thus be seen that a need exists for a mastitis treatment cannula assembly which will accurately, positively, and reproducibly limit the depth of cannula insertion while not increasing treatment time, cost or the risk of contamination. Additionally, there exists a need for a cannula assembly that provides the option of full insertion for those cows in which the 3 to 4 mm depth is impractical. The two part mastitis cannula cap assembly of the present invention provides a very satisfactory solution to these problems.

SUMMARY OF THE INVENTION

It is a primary object of the present invention to provide a cannula cap for use with a mastitis (intramammary) infusion syringe.

A principal object of the present invention is to provide a mastitis (intrammary) cannula cap having the capability of limiting the insertion depth of the syringe cannula into the cows'teat canal.

A further object of the present invention is to provide a mastitis cannula cap that is comprised of two separable parts.

Still another object of the present invention is to provide a removable outer cap that, when detached, will expose a limited portion of the mastitis syringe cannula and provide contact surfaces that will not damage the teat.

Yet another object of the present invention is to provide a two part mastitis cannula cap in which the proximal part of the cap (the inner cap) permits only a portion of the cannula to enter the cow's teat canal.

Still a further object of the present invention is to provide a two part mastitis cannula cap which will allow a herdsman the option of partial insertion of the teat canal, when only the outer cap is removed, or, full cannula insertion when both the inner cap and the outer cap are removed.

Even yet a further object of the present invention is to provide a two part mastitis cannula cap in which the outer cap or the entire two part cap may be readily detached from the mastitis syringe with the aid of only the operator's fingers.

Still yet an additional object of the present invention is to provide a two part mastitis cannula cap which does not leak, prevents contamination of the cannula during storage and will not damage the surface of the mastitis syringe cannula.

A still further object of the present invention is the provision of a two part mastitis cannula cap in a unibody construction prior to use so that no leakage or contamination of the contents of the syringe can occur during storage.

Another object of the present invention is the provision of a breakaway seal between inner and outer cap portions of the cannula cap.

A still further object of the invention is the provision of an internal seal to prevent leakage and contamination of syringe contents.

As will be discussed in greater detail in the description of the preferred embodiments, which is set forth subsequently, the two part mastitis cannula cap assembly in accordance with the present invention includes an inner cap which snaps onto the base of the cannula at the first end, and which has a relatively wide outer or distal end to prevent accidental insertion into a teat orifice and an outer cap which is removably attached or carried on the distal end of the inner cap. The outer cap covers generally about the outer 3 to 4 mm of the mastitis syringe cannula which extends through an aperture at the distal end of the inner cap and, when removed, allows only partial depth insertion of the cannula into the teat canal. This depth of insertion is limited by the relatively large diameter of the distal end of the inner sleeve which also stabilizes the cannula against the teat end and helps to prevent leakage during infusion of the treatment materials during utilization of the partial insertion technique.

One embodiment of this invention includes an outer circumferential rim or flange which is formed as a part of the outer cap and which facilitates easy removal of this first cap.

In another embodiment of the two part cap invention, a twist-off or pull-off outer cap is secured to the inner cap. The outer cap can also be broken off by applying a lateral force, or can be ripped or torn off by, e.g. using the teeth. Raised ridges on the outside surface of the entire cannula cap serve to facilitate the grasping and removal of the outer cap by a herdsman, veterinarian or user. As with the embodiment described above, when the outer cap is removed, approximately 3 to 4 mm of the mastitis syringe cannula is exposed and infusion into the teat canal is limited by the relatively wide diameter of the inner cap.

It is to be understood that the forms of the present invention herein shown and described are to be taken as preferred embodiments. Various changes may be made in size, shape and arrangement of the parts without departing from the scope of the subjoined claims. For example, the method of separation of the cap segments may be made by means other than those illustrated in the drawings. However, these are within the scope of the purpose of the invention, i.e. limiting the depth of penetration into the teat canal.

By use of this invention, the herdsman or the like who is responsible for the treatment of the cattle can readily remove the outer cap, expose only approximately 3 to 4 mm of cannula required for partial insertion, and effect infusion of the treatment material in an efficient, safe, and predictable manner.

In operation, the herdsman or user removes the outer cap using his thumb and forefinger to grasp the relatively wide outer rim or, in another embodiment, the ribbed projections of the outer cap. The cap is taken off by pull, pull combined with rotation or by bending to break off the cap. This exposes approximately 3 to 4 mm of the syringe cannula which is then inserted into the cow's relatively longer (5 to 10 mm) teat canal and the contents of the syringe infused into the cow udder. The depth of insertion into the teat canal is limited to a portion of the cow's teat canal by the relatively wide inner cap; thereby allowing the antibiotic to be infused into the udder without damaging the keratin lining of the teat canal, without dilating the entire length of the teat canal, without transporting bacteria into the teat cistern, and allowing antibiotic to be placed in contact with bacteria within the teat canal. Since the depth of the insertion is controlled by the abutment of the wide diameter of the distal end of the inner cap, there is no chance for insertion beyond the approximately 3 to 4 mm teat canal insertion depth. Thus partial, therapeutic insertion into the teat canal is consistently and readily achieved with this device.

When the outer cap is in place, for example, during storage at the dairy farm, a protective seal is created over the cannula, preventing contamination from the environment while also preventing leakage of the contents of the syringe.

Should a full insertion procedure be desired, the complete cap assembly can be removed from the cannula by separation of the first or proximal end of the inner cap from the base of the cannula generally as has been accomplished in the past. Once the inner cap and outer cap has been removed to expose the full length of the cannula, full insertion can be done in the conventional manner. Thus the two part mastitis cannula cap in accordance with the present invention provides the user with a choice. He can remove only the outer cap and utilize the cannula in a partial insertion treatment procedure, or he can remove both the inner cap and outer cap to expose the full length of the mastitis control cannula for a full insertion procedure.

The two part cap may be sized so as to be usable with existing mastitis treatment cannula and syringe assemblies, is not expensive to manufacture and is thus disposable, and provides treatment flexibility not previously available. The two part mastitis cannula cap of the present invention is a significant advance in the art and is an effective tool in the control of bovine mastitis.

BRIEF DESCRIPTION OF THE DRAWINGS

While the novel features of the two part mastitis cannula cap in accordance with the present invention are set forth with particularity in the appended claims, a full and complete understanding of the invention may be had by referring to the detailed description of preferred embodiments as is set forth hereinafter and as illustrated in the accompanying drawings in which:

FIG. 1 is a side elevation view, partly in section, of a mastitis treatment syringe and cannula utilizing the two part cap of the present invention;

FIG. 2 is a cross sectional view of the cannula and cap assembly taken along line II—II of FIG. 1; and FIG. 3 is an enlarged cross sectional side view of a portion of the outer and inner caps of the present invention.

DESCRIPTION OF THE PREFERRED EMBODIMENTS

Figure 4A:
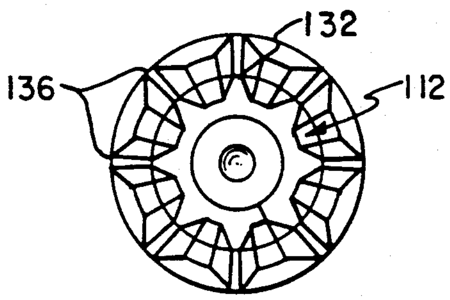
FIG. 4*a* is a cross sectional view and FIG. 4*b* a side elevation view, partly in section, of a mastitis treatment syringe and cannula illustrating a second more preferred embodiment (twist-off version) of the two part cap of the present invention.

Turning initially to FIG. 1, a first embodiment of a two part mastitis cannula cap 10, in accordance with the present invention is presented. Two part cap assembly 10 includes an outer or overcap 12 and an inner cap 14. This two part mastitis cannula cap is shown in FIG. 1 in conjunction with a typical mastitis infusion syringe 16 that conventionally is a 5 ml or 10 ml disposable plastic syringe which is intended for a one time usage. A proximal or first end of an insertion cannula 18 is integrally molded with a reduced diameter end 20 of syringe 16. Insertion cannula 18 typically is 20 to 25 mm in length and has a generally cylindrical hollow body 22 with a through bore 24. A generally conical shaped hub 26 is formed at first or distal end 28 of cannula 18 and this hub 26 is fused to the reduced diameter end 20 of syringe 16. An annular groove 30 is formed in the end 20 of syringe 16 adjacent cannula hub 26. This syringe 16 and cannula 18 assembly is a typical configuration in which a bovine mastitis treatment material is supplied. While the two piece mastitis cannula cap in accordance with the present invention will be discussed for use with this syringe and cannula assembly, it will be understood that the size of the syringe, the overall length of the cannula and other similar structural characteristics of this syringe and cannula assembly, which form no part of the subject invention, could be changed or modified.

Two part mastitis cannula cap 10 includes, as was indicated above, an outer cap 12 and an inner cap 14. As may be seen in FIG. 1, outer cap or overcap 12 is somewhat capshaped and has a generally cylindrical sidewall 32. A somewhat planar end wall 34 of outer cap 12 is joined to a first end of cylindrical sidewall 32 and has a central projection 36 which forms an interior concavity 38 that receives a free end or distal tip 40 of the insertion cannula 18. Concavity 38 has a depth of generally about 3 mm, depending on the length of free end 40 of cannula 22 which extends beyond inner cap 14, in a manner to be discussed shortly. Concavity 38 and cannula tip 40 are cooperatively sized to form a snug, leak resistant interfit. An enlarged annular outer flange 42 is joined to outer cap 12 at the second end of sidewall 32 opposite planar endwall 34. This outer flange 42 should be sufficiently large to facilitate grasping of outer cap 12 when this outer 12 is to be removed from inner cap 14. In this embodiment, this annular outer flange 42 may have a diameter of generally about 10 to 20 mm.

Inner cap 14, as may be seen most clearly in FIG. 1, is generally in the shape of an elongated cylindrical sleeve having a tubular sidewall 50. A snap end 52 of inner cap 14 has a radially inwardly extending lip 54 that is receivable in annular groove 30 formed at the junction of syringe end 20 and hub 26 of cannula 18. Detachment of the snap end 52 of inner cap 18 from syringe 16 is achieved by bending inner cap 14 to unseat lip 54 from groove 30.

Inner cap 14 terminates at its distal end 56 in an outer end face 58 that has a central aperture 60 through which the free end 40 of insertion cannula 18 passes. The outer end face 58 of inner cap 14 has a relatively wide diameter, generally in the range of about 3 to 12 mm, preferably about 5 to 7 mm and is smooth and somewhat rounded at its peripheral edges 62.

Outer cap 12 overlies the distal end 56 of inner cap 14, as may be seen in FIGS. 1 and 3. An inner surface 70 of outer cap sidewall 32 slidingly cooperates with an outer surface 72 of tubular sidewall 50 of inner cap 14 to effect retention of outer cap 12 on the distal end 56 of inner cap 14. Securement of inner cap 14 to outer cap 12 is enhanced by the cooperation of a pair of opposed protrusions 76, formed on the outer surface 72 of tubular inner cap sidewall 50, with a circumferential recess 80 cooperatively located in the inner surface 70 of outer cap sidewall 32. Alternatively, the number of protrusions 76 could be increased or a continuous rim (not shown) could be substituted. These protrusions 76, or rim, and circumferential recess 80 are sized so that a pulling or pushing force exerted on outer cap annular flange 42 will effect separation of outer cap 12 from inner cap 14 and not separation of inner cap 14 from syringe end 20. Separation of inner cap 14 from syringe end 20 is more easily accomplished by grasping the tubular sidewall 50 of inner cap 14 and by utilizing a bending force to unseat lip 54 from groove 30. Thus the two separating forces are of differing types so that separation will occur at the desired point.

Another more preferred embodiment of the two part mastitis cannula cap 110 is illustrated in FIGS. **4*a* and 4*b* where the two part cap is designated and includes, an outer cap 112 and an inner cap 114. In these figures, elements identical with those in FIGS. 1–3 have the same identifying numbers. As may be seen in FIG. 4*b*, outer cap 112 has a cylindrically shaped sidewall 132 with ridge-like projections 136 that may be visualized on the FIG. 4*a* cross sectional view. Ridge-like projections 136 facilitate grasping of the outer cap. Outer cap 112 is physically joined to inner cap 114 by a thin breakaway seal 178 that completely surrounds but does not contact the distal teat cannula 18. Approximately 1 mm proximal to the breakaway seal 178 there exists a radial seal 139 that projects from tubular sidewall 150 of the inner sleeve 114. This radial seal 139 is snugly in contact with and somewhat compresses the insertion cannula 18, thereby preventing the contents of syringe from leaking out from the cap. Concavity 138 receives the free end or distal tip 140 of insertion cannula 18. Concavity 138 has a depth of generally about 3 to 4 mm, depending on the length of the free end 140 of cannula 22 which extends beyond inner cap 114** in a manner to be discussed shortly.

Inner cap 114, as may be seen most clearly in FIG. **4*b*, is generally in the shape of an elongated cylindrical sleeve having a tubular sidewall 150. The outside of sidewall 150 is embossed with 1/16 inch raised ridges 136 (in a manner similar to the outer cap) which serve to facilitate grasping of the inner cap 114. A snap end 152 of inner cap 114** has a radially inwardly extending lip 154 that is receivable in annular groove 30 formed at the junction of syringe end 20 and hub 26 of cannula 18. Detachment of the snap end is performed in the same manner as in the first embodiment.

Also as in the first embodiment, inner cap 114 terminates at its distal end in an outer end face 158 that has a central aperture 160 through which the free end 140 of insertion cannula 18 passes. The outer end face 158 of inner cap 114 is planar or slightly convex or bevelled and has a relatively wide diameter, generally in the range of about 3 to 12 mm, preferably about 5 to 7 mm and is smooth and somewhat rounded at its peripheral edges 162.

Figure 4B:
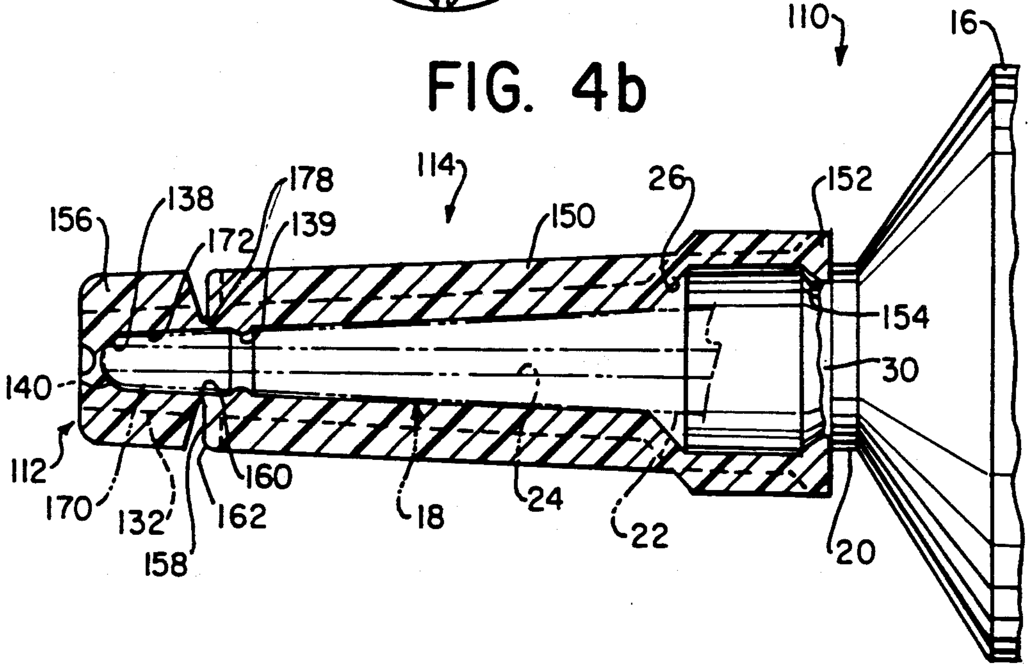

In FIG. 4*b*, the inner sidewall 170 of the outer cap 112 slidingly cooperates with the outer surface of the distal cannula 172. The inner wall 170 of the outer cap 112 forms the breakaway seal 178 between the inner cap 114 and outer cap 112. The thickness of the breakaway seal 178 is of sufficient strength to maintain a closure between the inner cap 112 and outer cap 114 providing protection against cannula damage or contamination during shipment or storage. The seal 178, however, is thin enough to allow the herdsman to readily separate the outer cap 112 from the inner cap 114 at the junction located at central aperture 160, resulting in a smooth surface on the distal plane 158 of the inner sleeve 114. Separation is facilitated by the traction provided by raised ridges 136 on the outside walls of the entire device 110.

Separation of inner cap from syringe end is effected as in the first embodiment. That is, the tubular sidewall 150 of inner cap 114 is grasped and a bending force to unseat lip 154 from groove 30 is utilized. Thus in both embodiments the two separating forces are of differing types so that separation will occur at the desired point.

As described in a previous section, in use, the two part mastitis cannula cap assembly in accordance with the present invention allows the dairy farmer, veterinarian, herdsman, or the like to practice whichever infusion procedure he feels is appropriate for each teat canal of the udder. Should partial insertion be desired, the outer cap's 12 outer flange 42 in the first embodiment, or the ridges 136 of the outer cap 112 in the second embodiment, are grasped and the outer cap is removed by gently twisting, bending or applying a longitudinal force. This exposes the free or distal end of insertion cannula which is slowly inserted into the teat orifice and passed proximally into the teat canal. In accordance with present procedures, generally about 3 to 4 mm of the cannula free end 40 (or 140) projects beyond the relatively wide diameter smooth end face 58 (or 158) of inner cap 14 (or 114). Since the teat canal of a cow is approximately 5 to 10 mm in length, the 3 to 4 mm projection of cannula free end 40 (or 140) and the wider diameter of the exposed distal end of the inner cap 58 (or 158) limits cannula insertion depth to a point within the teat canal and not into the teat cistern.

Thus partial cannula insertion to the correct depth can be quickly accomplished. The relatively large diameter and slightly bevelled or planar outer end face 58 (or 158) of the inner cap also serves to stabilize the infusion cannula against the teat end while the free end 40 (or 140) of the cannula is inserted partially into the teat canal. This wide planar, or slightly bevelled end face also minimizes leakage of the material being infused. Since removal of the outer cap 12 (or 112) produces a smooth and clean end face 58 (or 158) with gently rounded corners it will not harm the teat end. Additionally, since the teat canal is quite small in diameter, (0.6 to 1.6 mm), there is no possibility of the generally 3–12 mm, preferably 5–7 mm large diameter end face 58 (or 158) of the inner cap being inserted into the teat canal.

If full insertion of the mastitis treatment cannula is desired, this can readily be accomplished by removal of both the outer and inner caps as a single assembly. As discussed previously, this is accomplished by grasping the tubular sidewall 50 (or 150) of the inner cap 14 (or 114) and by exerting sufficient bending force to unseat the lip 54 (or 154) on the snap end or proximal end 52 (or 152) of the inner cap 14 from its cooperating groove 30 at the juncture of the syringe body 16 with the attached cannula 18. This exposes the entire length of cannula 18 so that full insertion of the cannula into the teat cistern through the teat canal can be accomplished.

It should be noted that the juncture of the syringe body with cannula 18 is secure enough that, in removing only the outer cap, the juncture does not break or unseat.

The overall length of the two part mastitis cannula cap of the present invention will be generally in the range of 25 to 40 mm. This dimension is determined by the length of the cannula and is not particularly critical in itself. The length of the inner cap 14 (or 114) with respect to the length of the cannula 18 is important because the difference in lengths between the shorter inner cap 14 (or 114) and the longer cannula 18 determines the length of cannula free end tip 40 (or 140) protrusion beyond the end face 58 (or 158) of inner cap 14 (or 114). As discussed above, a projection of generally about 3 to 4 mm is believed to be proper for optimal infusion of the mastitis treatment antibiotic preparation into the teat canal. The length of cannula tip 40 (or 140) projection, in turn, dictates the depth of interior concavity 38 (or 138) on the end wall 34 (or 156) of the outer cap 12 (or 112). In FIG. 1, the outer end of the distal tip 40 of cannula 18 should bear against the inner surface of this projection 36 to minimize any possible treatment material loss during shipment or handling and before the outer cap 12 is removed, either by itself during partial insertion, or with inner cap 14 during full insertion. With the embodiment described in FIG. 4*b*, leakage of the syringe contents is prevented by the radial seal 139 that projects from the distal inner wall of the inner cap sleeve 150 against the outer wall of the cannula 22 and the break-away seal 178 between the inner and outer caps.

The embodiment of FIGS. 4*a* and 4*b* thus provides several distinct advantages to the dairymen. These features include:

1. The inner and outer caps are sealed together at the junction of the inner cap and the outer cap, forming a unibody cap. This unibody feature provides that an impermeable seal is formed which effectively eliminates the possibility of leakage of the syringe contents or contamination of the syringe cannula during storage.

The plastic seal between the inner and outer cap is designed to break away when sufficient tractional forces are applied by the dairyman. Raised ridges along the outer wall of the entire unibody cap facilitate this process. Thus the outer cap may be easily removed by the dairymen, exposing a portion of the syringe cannula. The resulting 3–4 mm exposed cannula provides the ideal depth of insertion of the mastitis syringe cannula. Additionally, since no additional device needs to be placed on the cannula, the risk of contaminating the cannula is significantly minimized.

2. The two-part cap is secured tightly to the syringe cannula assembly by a snap-lock fit at the hub of the cannula. This tight fit ensures that the entire cap will not snap off while the outer cap is being twisted off. However, should the dairymen choose to remove the entire unibody cap (to expose the full length of the cannula) this may be easily accomplished bending the entire unibody cap. Thus this design allows partial or full insertion to be easily practiced by the dairymen.

3. The radial seal 139 adjacent to the distal end of the inner sleeve serves to compress the syringe cannula just proximal to the breakaway seal. This sealing feature operates in cooperation with the breakaway seal to prevent any possible leakage of the syringe contents.

The two piece mastitis cannula cap in accordance with the present invention provides a safe, easy to use, sterile, accurately controllable and reproducible, disposable, inexpensive means to practice the partial cannula insertion technique which recent studies have suggested may enhance the effectiveness of the treatment of mastitis in dairy cows. At the same time, the two part cap structure affords the user an assembly which can be utilized for conventional full cannula insertion treatment, if desired. Thus, the two part mastitis cannula cap of the present invention provides the freedom to select and use whichever of the two treatment procedures is deemed more desirable without sacrificing ease of use, disposability, and package integrity.

While preferred embodiments of a two part mastitis cannula cap in accordance with the present invention have been set forth fully and completely hereinabove, it will be obvious to one of skill in the art that a number of changes in, for example the size and shape of the syringe, the materials used for the syringe, cannula and cap, the overall length of the cannula and hence the overall length of the two part cap and the like may be made without departing from the true spirit and scope of the present invention which is accordingly to be limited only by the following claims.

What is claimed is:

1. In combination with a mastitis infusion syringe having a blunt-tipped cannula sized in diameter and length to fit the teat canal portion of a teat of a dairy vow, a two part mastitis cannula cap for facilitating controllable length insertion of the mastitis infusion syringe into the teat canal portion of a teat of a dairy cow said cap comprising:

a hollow inner cap including a rear end having means to removably attach said inner cap to the syringe over the cannula and a forward end portion of which has a diameter size to prevent insertion of said inner cap into a teat canal, said forward end having an aperture dimensioned to receive the cannula in sealing engagement therein, means defining an extension of the cannula forward of said forward end, the length of said extension being substantially less than the full length of the cannula, whereby it is less than the length of a teat canal, and means defining a distal end surface closely surrounding said extension for engaging said teat upon insertion of the extension;

an outer cap for covering the cannula extension removably secured in covering relationship with respect to said extension; and whereby either the outer cap alone can be removed to expose the extension of the cannula for insertion into a teat canal for a distance less than full cannula length, or the outer and inner caps can be removed to expose the cannula for full insertion.

2. A two part mastitis cannula cap in accordance with claim 1, said cap further comprising:

breakaway means for securing and sealing said outer cap to said inner cap, said breakaway means subject to being broken away by an application of force to said outer cap; and sealing means in said cannula cap for preventing fluid leakage from said cannula cap.

3. The two part mastitis cannula cap of claim 2 wherein said outer and inner cap are made of plastic and said breakaway means includes a thin strip of plastic between outer cap and inner cap.

4. The two part mastitis cannula cap of claim 2 or 3 including ridges disposed along an outer surface of the outer cap to facilitate removal of said outer cap by twisting or pulling action.

5. The two part mastitis cannula cap of claim 4 including ridges also disposed along an outer surface of said inner cap to enable grasping of said surface during removal of said inner cap or outer cap.

6. A two part mastitis cannula cap in accordance with claim 26, said cap further comprising:

breakaway means for securing and sealing said outer cap to said inner cap, said means subject to being broken away by force applied to said outer cap.

7. The two part mastitis cannula cap of claim 6 wherein said distal end surface has a diameter of generally between 3 mm and 12 mm.

8. The two part mastitis cannula cap of claim 7 wherein said distal end surface has a diameter of generally between 5 mm and 7 mm.

9. The two part mastitis cannula cap of claim 6 wherein the length of said extension is about 3 to 4 mm.

10. The two part mastitis cannula cap of claim 6 wherein said distal end surface of said inner cap includes a rounded peripheral edge.

11. The two part mastitis cannula cap of claim 6 including ridges disposed along an outer surface of the outer cap to facilitate removal of said outer cap by twisting action.

12. The two part mastitis cannula cap of claim 6 including ridges also disposed along an outer surface of said inner cap to enable grasping of said surface during removal of said inner cap or outer cap.

13. The two part mastitis cannula cap of claim 6 wherein said breakaway means includes a thin ribbon of plastic material between the inner and outer caps.

* * * * *